(12) United States Patent
Barry et al.

(10) Patent No.: US 7,018,121 B2
(45) Date of Patent: Mar. 28, 2006

(54) COMBINED PAPER AND TRANSPARENCY SENSOR FOR AN IMAGE FORMING APPARATUS

(75) Inventors: Raymond Jay Barry, Lexington, KY (US); John Parker Richey, Lexington, KY (US); Michael David Maul, Lexington, KY (US); Steven R. Rehmel, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 0 days.

(21) Appl. No.: 10/798,127

(22) Filed: Mar. 11, 2004

(65) Prior Publication Data

US 2005/0201808 A1     Sep. 15, 2005

(51) Int. Cl.
*B41F 35/00* (2006.01)
*B41J 29/18* (2006.01)

(52) U.S. Cl. ............... 400/708; 400/703; 356/445; 356/446; 356/600; 399/45; 250/239

(58) Field of Classification Search ............... 400/718, 400/679
See application file for complete search history.

(56) References Cited

U.S. PATENT DOCUMENTS

| | | |
|---|---|---|
| 1,917,379 A | 7/1933 | Lowry |
| 3,360,652 A | 12/1967 | Bernous |
| 3,435,240 A | 3/1969 | Brunton |
| 3,522,739 A | 8/1970 | Coor et al. |
| 3,832,065 A | 8/1974 | Sullivan et al. |
| 3,910,701 A | 10/1975 | Henderson et al. |
| 4,428,041 A | 1/1984 | Honkawa |
| 4,540,887 A | 9/1985 | Minerd et al. |
| 4,685,982 A | 8/1987 | Kucheck |
| 4,779,988 A | 10/1988 | Horiguichi |
| 4,794,274 A | 12/1988 | Lohn |
| 4,975,571 A * | 12/1990 | McMurtry et al. ...... 250/231.16 |
| 4,983,854 A | 1/1991 | Mizuno et al. |
| 5,084,627 A | 1/1992 | Ueki et al. |
| 5,139,339 A | 8/1992 | Courtney et al. |
| 5,283,424 A | 2/1994 | Acquaviva et al. |
| 5,323,176 A | 6/1994 | Sugiura et al. |
| 5,329,338 A | 7/1994 | Merz et al. |
| 5,354,995 A | 10/1994 | Endo et al. |
| 5,608,207 A | 3/1997 | Allen et al. |
| 5,751,443 A | 5/1998 | Borton et al. |
| 5,754,213 A | 5/1998 | Whritenor |
| 5,764,251 A * | 6/1998 | Hashimoto ................... 347/16 |
| 5,852,299 A | 12/1998 | Kimura et al. |

(Continued)

*Primary Examiner*—Daniel J. Colilla
*Assistant Examiner*—Marissa Ferguson
(74) *Attorney, Agent, or Firm*—Coats and Bennett, PLLC

(57) ABSTRACT

A media sensor for an image forming apparatus is operative to sense and distinguish opaque, transparent or no media in a media path. In one embodiment, an optical source and detector are positioned on opposite sides of the media path, at an acute, non-zero angle with respect to a direction normal to the media path. In other embodiments, an optical source and detector are co-located on the same side of the media path with an optical barrier between them, and one or more reflective surfaces positioned on the opposite side. With no media in the media path, the detector receives a readily detectable amount of optical energy emitted by the source. For opaque media, the detector receives very little, if any, optical energy emitted by the source. For transparent media, the detector receives a level of optical energy between that in the cases of opaque media and no media.

6 Claims, 6 Drawing Sheets

U.S. PATENT DOCUMENTS

| | | |
|---|---|---|
| 5,925,889 A | 7/1999 | Guillory et al. |
| 6,006,668 A | 12/1999 | Rehmann |
| 6,018,164 A | 1/2000 | Mullens |
| 6,192,141 B1 | 2/2001 | Ahn |
| 6,217,168 B1 | 4/2001 | Elgee |
| 6,237,847 B1 | 5/2001 | Milne |
| 6,255,665 B1 | 7/2001 | Elgee et al. |
| 6,291,829 B1 | 9/2001 | Allen et al. |
| 6,325,505 B1 | 12/2001 | Walker |
| 6,364,556 B1 | 4/2002 | Barbera et al. |
| 6,386,669 B1 | 5/2002 | Scofield et al. |
| 6,386,676 B1 | 5/2002 | Yang et al. |
| 6,400,912 B1 | 6/2002 | Tanaka et al. |
| 6,425,650 B1 | 7/2002 | Walker et al. |
| 6,433,329 B1 | 8/2002 | Butka et al. |
| 6,462,822 B1 | 10/2002 | Haines et al. |
| 6,464,414 B1 | 10/2002 | Washnock |
| 6,557,965 B1 | 5/2003 | Walker et al. |
| 6,561,643 B1 | 5/2003 | Walker et al. |
| 6,585,341 B1 | 7/2003 | Walker et al. |
| 2002/0005497 A1 | 1/2002 | Sano |
| 2002/0043614 A1 | 4/2002 | Miyamoto et al. |
| 2003/0001939 A1 | 1/2003 | Scofield et al. |
| 2003/0016085 A1 | 1/2003 | Yamazaki |
| 2003/0043365 A1* | 3/2003 | Ross et al. .................... 356/71 |
| 2003/0044189 A1 | 3/2003 | Okitsu et al. |

* cited by examiner

COMBINED PAPER AND TRANSPARENCY SENSOR FOR AN IMAGE FORMING APPARATUS

BACKGROUND

The present invention relates generally to the field of image forming devices and in particular to a media sensor for sensing and distinguishing between no media, opaque media, and transparent media.

To ensure high quality image formation, precise control of the speed and position of media sheets is required as they are transported within an image forming apparatus, for example, to ensure accurate registration of various color plane images applied separately to the media sheet. In addition, many parameters of the image-forming process, such as the media sheet transfer speed, the operating temperature of a fuser, and the like, depend on the type of media. For example, opaque media such as bond paper may require different image formation and fixing parameters than other media, such as transparencies. Hence, it is critical that both the position and the type of media sheet (e.g., opaque sheet or transparency) be accurately sensed.

A wide variety of media sensors are known in the art. In general, a media sensor may comprise an electro-mechanical contact that is made or broken when a media sheet trips a mechanical lever disposed in the media sheet path; an optical sensor whereby a media sheet blocks, attenuates, or reflects optical energy from an optical source to an optical detector; an opto-mechanical sensor, or other sensor technology, as well known in the art.

In practice, a given image forming apparatus may employ a plurality of media sensors. For example, two or more media sensors may be arrayed across the media path in a direction perpendicular to the media sheet transfer direction, to detect the media sheet width. As another example, many image-forming devices employ a first sensor to detect the position of a media sheet, and a second sensor to detect its type (e.g., opaque sheet or transparency). Both cost reduction and improved system reliability may be obtained by combining the functions of a plurality of sensors into a single, compact, integrated media sensor capable of sensing both the position and type of media sheets.

SUMMARY

The present invention relates to a media sensor for sensing media in the media path of an image forming apparatus. The sensor includes an optical source disposed at an acute, non-zero angle with respect to a direction normal to the media path, and an optical detector disposed at an acute, non-zero angle with respect to a direction normal to the media path, such that an optical path from the source to the detector passes through the plane of said media path. The sensor is operative to distinguish between no media, opaque media, and transparent media in the media path by detecting a level of optical energy in the case of transparent media that is between that in cases of no or opaque media.

In one aspect, the media sensor includes an optical source disposed on a first side of the media path and an optical detector disposed on a second side of the media path, in a spaced relationship with the optical source, such that the optical path from the source to the detector is disposed at an acute, non-zero angle from a direction normal to the media path. The sensor is operative to distinguish between no media, opaque media, and transparent media in said media path by detecting a level of optical energy in the case of transparent media that is between that in cases of no or opaque media.

In another aspect, the media sensor includes an optical source and an optical detector disposed in a spaced relationship with the optical source, the source and detector both disposed on a first side of the media path. The media sensor also includes an optical barrier disposed between the optical source and the optical detector. At least one reflective surface is disposed on a second side of the media path, the reflective surface(s) positioned to reflect optical energy from the optical source to the optical detector. The sensor is operative to distinguish between no media, opaque media, and transparent media in said media path by detecting a level of optical energy in the case of transparent media that is between that in cases of no or opaque media.

DETAILED DESCRIPTION OF THE INVENTION

Figure 1:
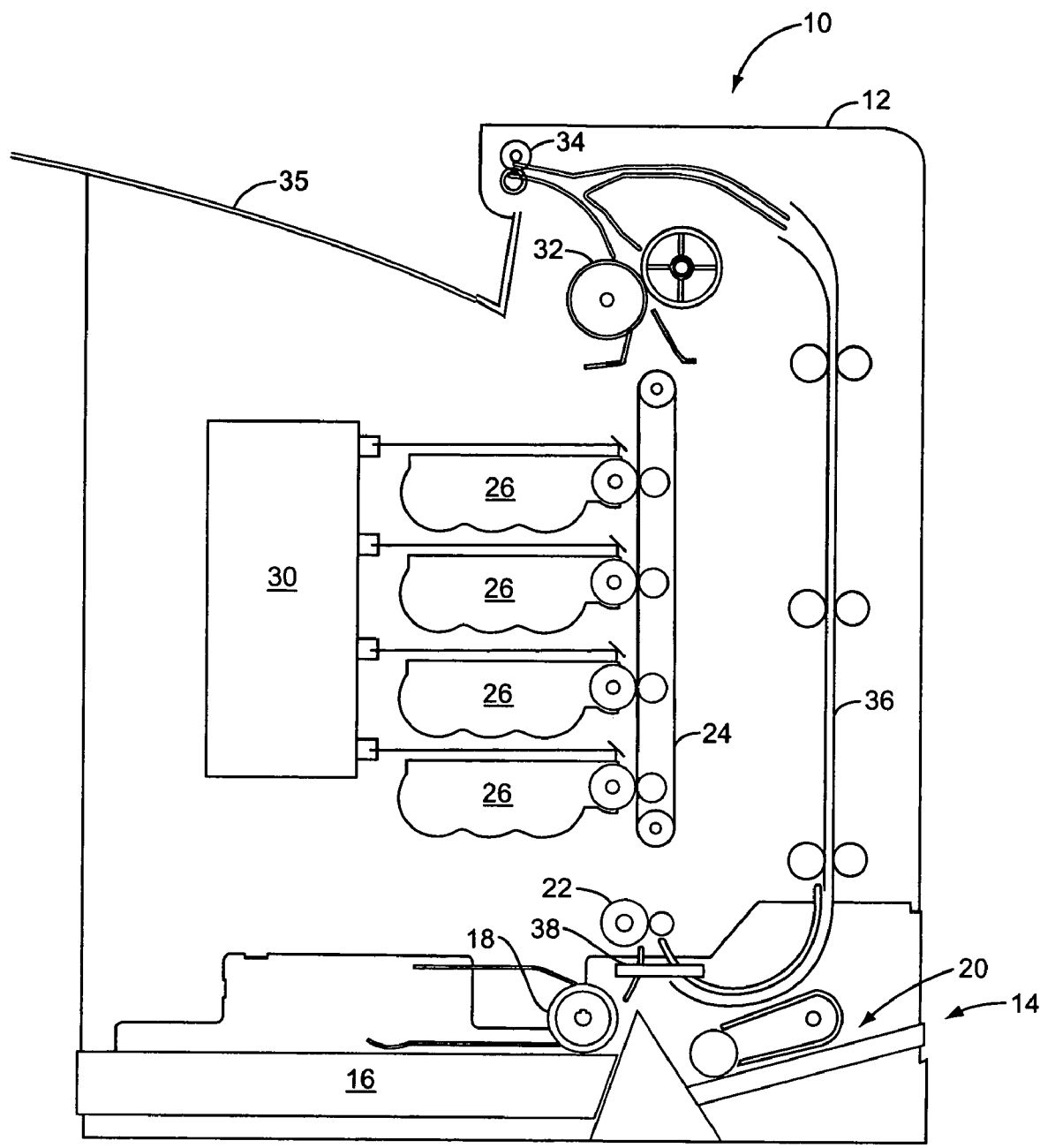
FIG. 1 is a functional block diagram of an image forming apparatus.

FIG. 1 depicts a representative image forming apparatus, indicated generally by the numeral 10. The image forming apparatus 10 comprises a housing 12 and a media tray 14. The media tray 14 includes a main media sheet stack 16 with a sheet pick mechanism 18, and a manual input 20. The media tray 14 is preferably removable for refilling, and located on a lower section of the device 10.

Within the image forming apparatus body 12, the image forming apparatus 10 includes a media sensor 38, registration rollers 22, a media sheet transfer belt 24, one or more removable image formation cartridges 26, an imaging device 30, a fuser 32, reversible exit rollers 34, and a duplex media sheet path 36, as well as various rollers, actuators, sensors, optics, and electronics (not shown) as are conventionally known in the image forming apparatus arts, and which are not further explicated herein.

The internal components of removable image formation cartridges 26 are not depicted in FIG. 1, but are briefly described. Each image formation cartridge 26 is a removable cartridge that may include a reservoir holding a supply of toner, a developer roller for applying toner to develop a latent image on a photoconductive drum, and a photoconductive (PC) drum, which may comprise, for example, an aluminum hollow-core drum coated with one or more layers of light-sensitive organic photoconductive materials. The image formation cartridge 26 may additionally include various rollers, paddles, augers and blades, as well known in the art. Note that this description is representative only—various image formation devices may organize these components into a plurality of cartridges.

In a typical color electrophotographic printer, three or four colors of toner—cyan, yellow, magenta, and optionally black—are applied successively to a print media sheet to create a color image. Correspondingly, FIG. 1 depicts four image formation stations, each including an image formation cartridge 26, arrayed along the media sheet transfer belt 24. To ensure the proper positioning of a media sheet, and the proper sequence of operations as it is transported past the four image forming stations, various media sensors 38 are utilized. According to the present invention, the media sensor 38 may be of a type described herein with respect to media sensors 40, 50, 60, that is operative to sense and distinguish between the conditions of no media, opaque media, or transparent media in the media path. It is important to note, however, that the media sensors of the present invention are not limited to electrophotography. Rather, the media sensors may be advantageously utilized in any image forming apparatus.

The operation of the image forming apparatus 10 is conventionally known. Upon command from control electronics, a single media sheet is "picked," or selected, from either the primary media stack 16 or the manual input 20. Alternatively, a media sheet may travel through the duplex path 36 for a two-sided print operation. Regardless of its source, the media sheet is presented at the nip of a registration roller 22, which aligns the sheet and precisely controls its further movement into the print path.

The media sheet is detected by the media sensor 38 (or a combination of media sensors 38), which preferably determine both the position and type of media. The image forming apparatus then sets up the proper timing and sequencing of subsequent image forming operations to match the media type. The media sheet then passes the registration roller 22 and electrostatically adheres to transport belt 24, which carries the media sheet successively past the image formation cartridges 26. At each image formation cartridge 26, a latent image is formed by the imaging device 30 and optically projected onto the PC drum. The latent image is developed by applying toner to the PC drum. The toner is subsequently deposited on the media sheet as it is conveyed past the image formation cartridge 26 by the transport belt 24.

The toner is thermally fused to the media sheet by the fuser 32, and the sheet then passes through reversible exit rollers 34, to land facedown in the output stack 35 formed on the exterior of the image forming apparatus body 12. Alternatively, the exit rollers 34 may reverse motion after the trailing edge of the media sheet has passed the entrance to the duplex path 36, directing the media sheet through the duplex path 36 for the printing of another image on the back side thereof. Again, while this description applies to the electrophotographic printer of FIG. 1, the media sensor 38 of the present invention is not limited to such an application.

Figure 2:
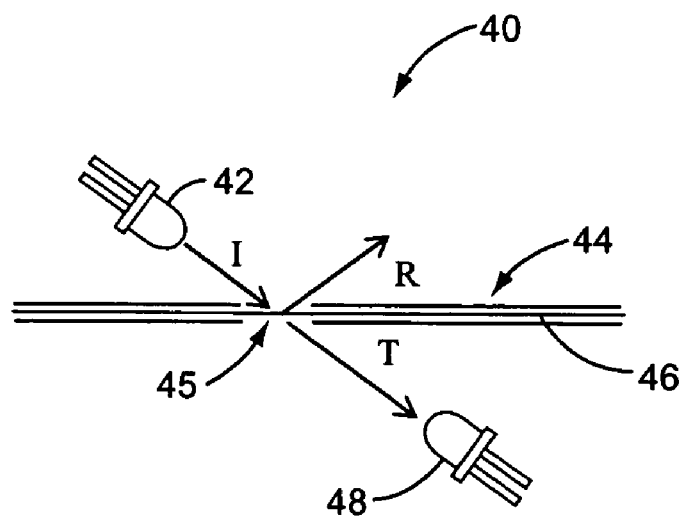
FIG. 2 is a functional block diagram of a media sensor according to one embodiment of the present invention.

FIG. 2 depicts a media sensor according to one embodiment of the present invention, indicated generally by the numeral 40. The media sensor 40 comprises an optical source 42 disposed on one side of the media path 44, at an acute, non-zero angle with respect to the direction normal to the media path 44. The optical source 42 emits optical energy, depicted in FIG. 2 as the incident light ray I. With no media present in the media path 44, the incident optical energy I passes through a gap or hole 45 formed in the media path 44 and strikes the optical detector 48. The optical detector 48 is aligned in light-receiving relationship with the optical source 42. That is, the optical detector 48 is disposed on the opposite side of the media path 44 from the source 42, at an acute, non-zero angle with respect to the direction normal to the media path 44. When no media sheet is present in the media path 44, the optical detector 48 receives most of the optical energy I emitted by the optical source 42.

In the case that opaque media 46 is present in the media path 44, most of the incident optical energy I emitted by the optical source 42 will be reflected from the surface of the media 46, as indicated by the light ray R, or alternatively absorbed by the media 46. Thus, in the case of opaque media 46 in the media path 44, very little, if any, of the incident optical energy I emitted by the optical source 42 will reach the optical detector 48.

In the case of transparent media 46 in the media path 44, some of the incident optical energy I emitted by the optical source 42 will be reflected from the surface of the media 46, as indicated by the light ray R. Additionally, some of the incident optical energy I will pass through the transparent media 46 and will be transmitted to the optical detector 48, as indicated by the light ray T. Assuming that the incident light I is randomly polarized and the surface of the transparent media 46 is smooth, the fraction of transmitted light T can be determined from Maxwell's equations and geometrical optics. In general, T depends on the angle of incidence of the light ray I with respect to the normal direction of the transparent media 46, and properties of the transparent media 46, including the index of refraction, the coefficient of absorption, and the thickness.

Figure 3:
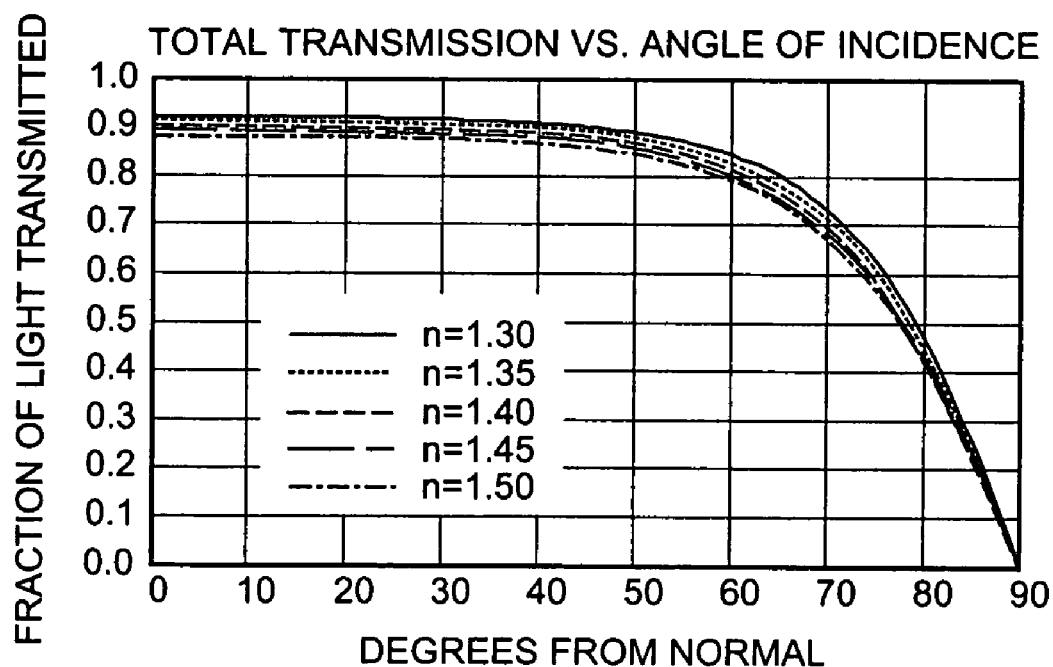
FIG. 3 is graph of theoretical light transmission attenuation as a function of angle of incidence.

FIG. 3 depicts a graph of the theoretical relationship between the transmitted optical energy T, as a fraction of the incident optical energy I, versus the angle of incidence (measured from the direction normal to the media 46) of the incident optical energy I with respect to the transparent media 46, for various values of n, the index of refraction.

Figure 4:
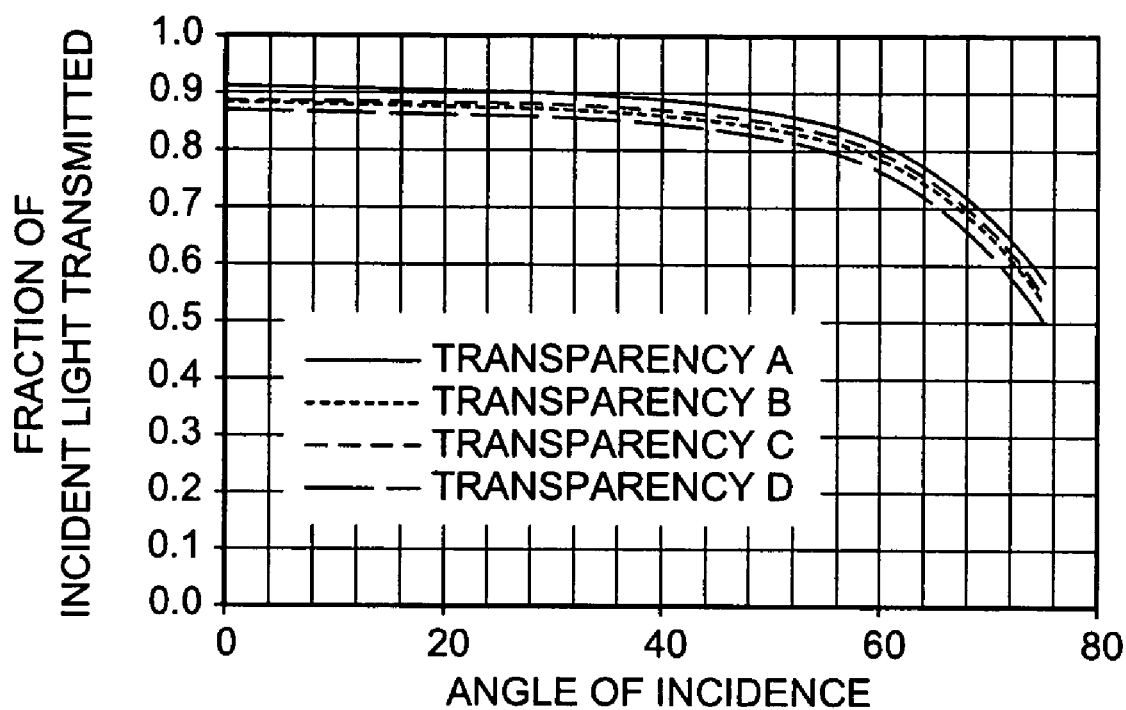
FIG. 4 is a graph of measured light transmission attenuation as a function of angle of incidence.

Experimentation verifies the theoretical results. FIG. 4 is a graph plotting the actual measurement of transmitted optical energy T, as a fraction of incident optical energy I, for various angles of incidence, and for different transparent media 46. The magnitude of the transmitted optical energy T depends primarily on the index of refraction of the transparent media 46 and the angle of incidence, because absorption by the transparent media 46 is small. As FIGS. 3 and 4 confirm, until the angle gets very large, the angle of incidence is not a major factor in determining the amount of light T transmitted. The angle of incidence is fixed by the physical positioning of the optical source 42 and optical detector 48 with respect to the media path 44. Additionally, the index of refraction of transparent media 46 is fairly stable, as it varies only slightly between the different transparent media 46 available. As both the index of refraction and the angle of incidence are stable and consistent parameters, the percentage of transmitted optical energy T through a transparency is likewise a stable and consistent parameter. The presence of transparent media 46 may thus be reliably detected by sensing an optical energy level greater than the case of opaque media 46 (which blocks or reflects more than 80% of the incident optical energy I at any angle of incidence), yet less than the case of no media in the media path 44.

In general, the optical source 42 may generate any color or intensity of light. The optical source 42 may generate monochromatic and/or coherent light, such as for example, a gas or solid-state laser. Alternatively, the light source 42 may emit non-coherent light of any color or mix of colors, such as any of a wide variety of visible-light, infrafred or ultraviolet light emitting diodes (LEDs) or incandescent bulbs. Preferably, the optical source 42 generates optical energy in the infrared range, and is most preferably an infrared LED. The optical detector 48 may comprise any sensor or device operative to detect and quantify optical energy emitted by the optical source 42. For example, optical detector 48 may comprise a photodiode, and preferably comprises a phototransistor. As silicon phototransistors are generally more sensitive at infrared wavelengths, an infrared LED optical source 42 and a silicon phototransistor optical detector 48 are presently preferred components, although the present invention is not limited to these elements.

As depicted in FIG. 4, any angle of incidence from 0° (i.e., normal to the plane of the media 46) to about 75° will result in transmitted optical energy T of sufficient magnitude to be detected and distinguished from opaque media 46. Restricting the angle of incidence from about 30° to about 65° confines the optical energy T to a range of about 70% to about 90% of the incident optical energy I. The most preferable range is about 55° to about 65°, and the most preferable angle of incidence is about 60°, which provides about 20% attenuation of the incident optical energy I. This value of transmitted optical energy T—about 80% of the incident optical energy I—is readily discernible from both the cases of opaque media 46 and no media.

In order to distinguish the three conditions (no media, transparent media 46 and opaque media 46), the optical detector 48 is preferably operated in a linear region. To ensure this, the optical detector 48 should be calibrated to eliminate or minimize the effects of component tolerances, component aging, temperature, contamination by toner or paper dust, and the like. Calibration procedures are well known in the art, and are not further discussed herein.

As the media sensor 40 reliably distinguishes the three conditions of no media present in the media path 44, opaque media 46 and transparent media 46, the sensor may separately sense the leading and trailing edges of the media 46. That is, for both opaque and transparent media 46, the sensor 40 will reliably detect when the media sheet 46 first passes the sensor position (leading edge) and when it clears the sensor position (trailing edge). In particular, the leading edge is indicated by a transition from a sensor output indicative of no media to a sensor output indicative of the presence of a media sheet (either opaque or transparent). The trailing edge is indicated by a transition from a sensor output indicative of either opaque or transparent media to a sensor output indicative of no media in the media path 44. This information may be combined with the known speed of the media 46 and the elapsed time from leading to trailing edge to determine the length of the media sheet 46, as well as its type and position.

Figure 5:
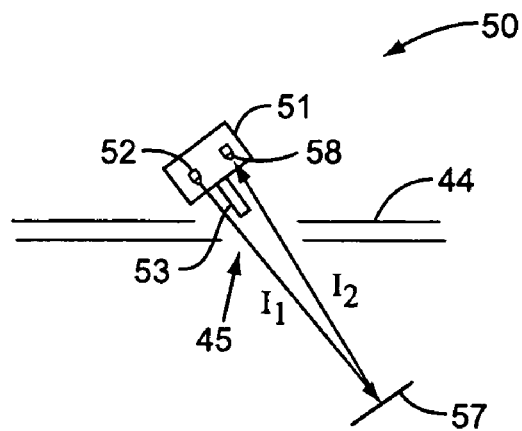
FIG. 5 is a functional block diagram of a media sensor according to one embodiment of the present invention, with no media in the media path.

FIG. 5 depicts a media sensor according to another embodiment of the present invention, indicated generally by the numeral 50. In the media sensor 50, an optical source 52 and optical detector 58 are co-located in a sensor body 51, in a substantially parallel, spaced relationship. The optical source 52 and optical detector 58 are thus positioned in the image-forming apparatus on the same side of the media path 44. The sensor body 51 is disposed at an acute, non-zero angle from the direction normal to the media path 44, as discussed above. The media sensor 50 includes an optical isolation barrier 53 that is effective to optically isolate the optical source 52 from the optical detector 58. That is, substantially none of the optical energy emitted by the optical source 52 directly reaches the optical detector 58.

In the case of no media in the media path 44, incident optical energy emitted by the optical source 52, represented by the light ray $I_1$, passes through a gap 45 in the media path 44 and strikes a reflective surface 57, disposed on the opposite side of the media path 44 from the sensor body 51. The angle of the reflective surface 57 is fixed such that the optical energy of the incident beam $I_1$ is reflected, represented in FIG. 5 by the light ray $I_2$, to the optical detector 58 disposed in the sensor body 51. Note that the optical barrier 53 does not impede or attenuate the reflected optical energy $I_2$. Thus, with no media present in the media path 44, the optical detector 58 will receive a readily detectable amount of the optical energy emitted by the optical source 52.

Figure 6:
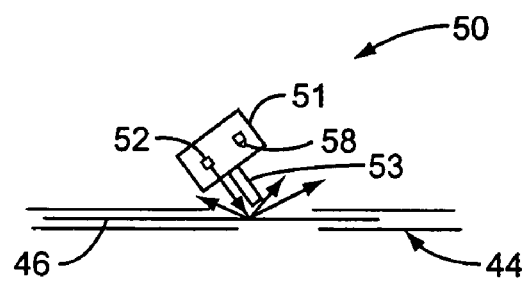
FIG. 6 is a functional block diagram of the media sensor of FIG. 5, with opaque media in the media path.

FIG. 6 depicts the case of opaque media 46 in the media path 44. Optical energy emitted by the optical source 52 strikes the surface of the opaque media 46, and is either reflected or absorbed. The opaque media 46 may be diffusely reflective (non-lustrous) or specularly reflected (shiny). In either case, both the position of the sensor body 51 at an angle with respect to the direction normal to the media 46 and the isolation barrier 53 ensure that over a wide range of system tolerances, very little, if any, optical energy reflected off of opaque media 46 will reach the detector 58. Thus, in the case of opaque media 46, very little of the optical energy emitted by the optical source 52 is received by the optical detector 58.

Figure 7:
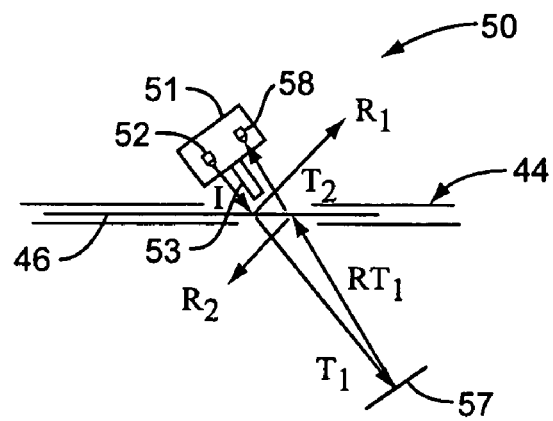
FIG. 7 is a functional block diagram of the media sensor of FIG. 5, with transparent media in the media path.

FIG. 7 depicts the case of transparent media 46 in the media path 44. Incident optical energy I emitted by the optical source 52 strikes the transparent media 46. Some of this light is reflected, as depicted by light ray $R_1$, and the rest is transmitted, as depicted by light ray $T_1$. Most of the reflection from transparencies is specular, so the angle of reflection will equal the angle of incidence. With the sensor body 51 positioned at an angle away from the normal axis, and additionally by virtue of the isolation barrier 53, substantially no specularly reflected light will strike the optical detector 58. Transmitted light T1 continues on to the reflective surface 57, where it is reflected back toward the optical detector 58, as depicted by light ray $RT_1$. Before it reaches the optical detector 58, the optical energy $RT_1$ again encounters the transparent media 46, where a portion is reflected away from the detector, as represented by light ray $R_2$, and the rest is transmitted, represented by light ray $T_2$, where it impinges upon the optical detector 58.

Compared to the case of no media present in the media path 44, the magnitude of optical energy $T_2$ reaching the optical detector 58 is reduced from that of the incident optical energy I by two encounters with the transparent media 46. The light transmission curves of FIG. 4 are relevant, with the percentage attenuation for each pass through the transparent media 46 multiplied. That is, for a given level of energy of transmitted optical energy T (expressed as a percentage of incident light I transmitted by the transparent media 46), light reaching the detector following two trips through the transparent media 46 is reduced to $T^2$ percent of I. For example, if 90% of incident light is transmitted by the transparency, then following two trips through the transparency, the light has been reduced to 81% of its incident intensity.

The media sensor 50 is compact, requiring little space in the image forming apparatus. Additionally, by positioning the optical source 52 and optical detector 58 on the same side of the media path 44, the task of routing cables to all of the active components is minimized. The discussion above regarding preferred components, calibration, and the like of media sensor 40 are fully applicable to the media sensor 50, with the exception that the preferred angle of incidence is between about 5° and about 40°, to account for the additional attenuation of optical energy caused by dual passes through the transparent media 46.

The media sensor 50 is operative to detect and distinguish the conditions of no media, opaque media 46, and transparent media 46 in the media path 44. In particular, with no media in the media path 44, the optical detector 58 will receive a readily detectable amount of the optical energy emitted by the optical source 52. With opaque media 46 in the media path 44, the optical detector 58 will receive very little of the optical energy emitted by the optical source 52. With transparent media 46 in the media path 44, the optical detector 58 will receive a level of optical energy greater than the case of opaque media, and less than the case of no media. In particular, for transparent media 46, the optical energy level received by the optical detector 58 is preferably attenuated by about 20% from that in the case of no media. The sensor 50 is operative to separately sense the leading and trailing edges of a media sheet 46, whether it is opaque or transparent.

Figure 8:
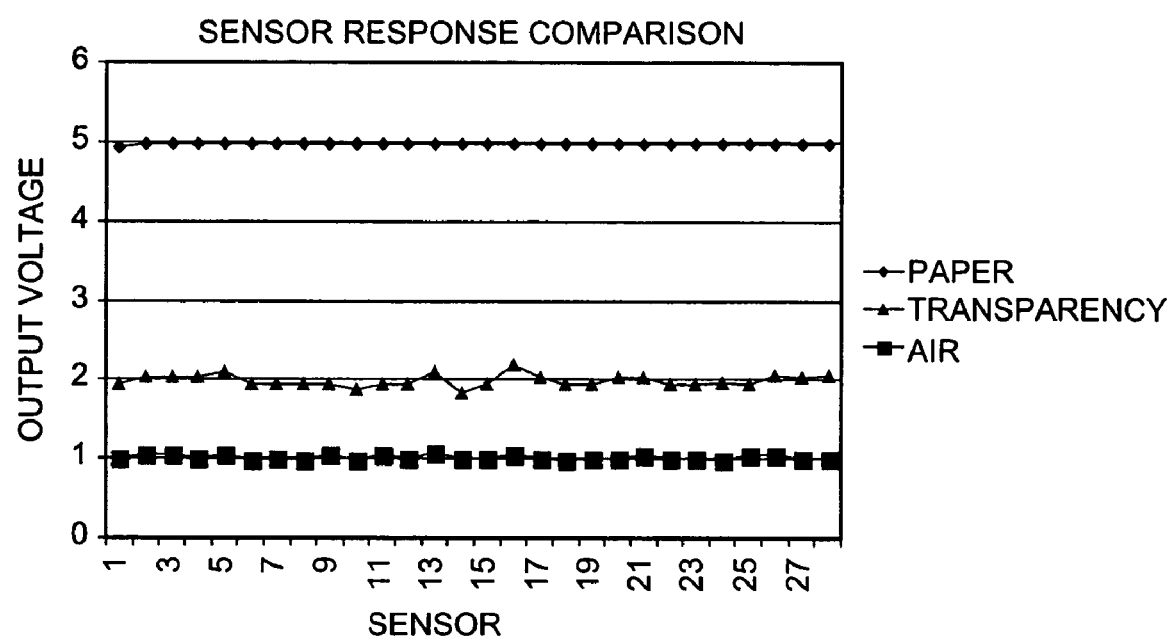
FIG. 8 is a graph of the output of media sensors detecting no media, opaque media, and transparent media.

FIG. 8 depicts a graph demonstrating the consistency of response of the media sensor 50 over a sample of 28 such sensors 50. Discriminating among these output levels of the sensor 50 to detect both the presence and type of media 46 is a straightforward exercise to those of skill in the electronics arts. Note that the units of the ordinate axis are volts, i.e., the output voltage of the media sensor 50. For the particular type and configuration of sensor 50 tested to generate the data of FIG. 8, the output voltage is inversely related to the intensity of optical energy at the optical detector 58. The relevant property depicted by FIG. 8, however, is that the sensor 50 output in the case of transparent media 46 is between, and reliably distinguishable from, the sensor 50 outputs in the cases of no media and opaque media 46.

Figure 9:
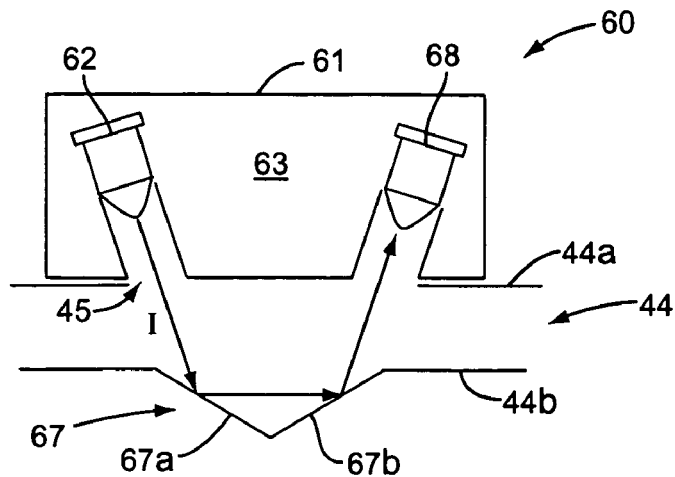
FIG. 9 is a functional block diagram of a media sensor according to one embodiment of the present invention, with no media in the media path.

FIG. 9 depicts a media sensor according to yet another embodiment of the present invention, indicated generally by the numeral 60. The media sensor 60 comprises an optical source 62 and optical detector 68 co-located in a sensor body 61. The optical source 62 and optical detector 68 are disposed within the sensor body 61 at equal and opposite acute, non-zero angles with respect to a normal direction from the media path 44 (when the sensor body 61 is mounted flush with the media path 44 as shown). In this configuration, all of the advantages of orienting the optical source 62 and optical detector 68 at an angle from the normal direction accrue, however, the sensor body 61 itself may be flush mounted to the upper media guide 44a of the media path 44 (over a hole 45 formed in the upper media guide 44a). The sensor body 61 includes an integral optical barrier 63, that effectively optically isolates the optical source 62 from the optical detector 68.

The media sensor 60 includes reflective surfaces 67, comprising reflective surface 67a and reflective surface 67b. Reflective surfaces 67a and 67b are preferably disposed at equal and opposite angles with respect to a direction normal to the plane of the media path 44, and preferably form a corner-cube retro-reflector. As well known in the optical arts, a fundamental property of a corner-cube retro-reflector is that an incident light ray I, regardless of its angle of incidence (within a limited range) is reflected at an equal and opposite angle. The reflective surfaces 67 are preferably formed as an integral part of the lower media guide 44b. Alternatively, a hole may be provided in the lower media guide 44b, and a separate reflective surface or surfaces 67 positioned on the opposite side of the media path 44 from the sensor body 61 so as to reflect optical energy emitted by the optical source 62 to the optical detector 68.

FIG. 9 depicts the case of no media present in the media path 44. Optical energy emitted by the optical source 62, indicated by the light ray I, travels through a hole 45 formed in the upper media guide 44a, through the media path 44, is successively reflected by reflective surfaces 67a and 67b, travels back through the media path 44, through the hole 45, and strikes the optical detector 68. In this case, the optical detector 68 receives a readily detectable amount of the optical energy I emitted by the optical source 62.

Figure 10:
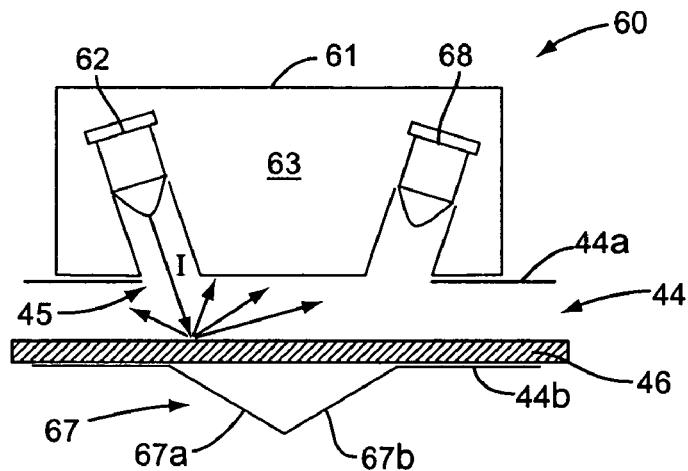
FIG. 10 is a functional block diagram of the media sensor of FIG. 9, with opaque media in the media path.

FIG. 10 depicts the case of opaque media 46 present in the media path 44. Optical energy I emitted by the optical source 62 passes from the sensor body 61, through the hole 45, and strikes the surface of the opaque media 46. As discussed above, the light is diffusely or specularly reflected from the surface of the opaque media 46 or alternatively is absorbed by the opaque media 46. In any case, the relative positions and angles of the optical source 62 and optical detector 68, and the integral optical barrier 63 of the sensor housing 61, ensure that very little, if any, optical energy I emitted from the optical source 62 reaches the optical detector 68.

Figure 11:
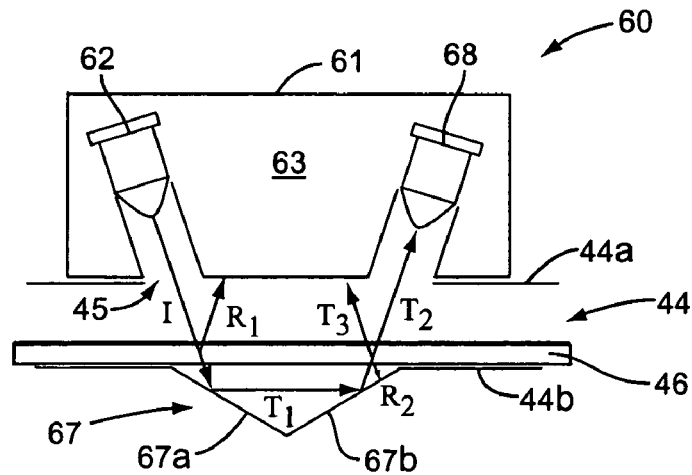
FIG. 11 is a functional block diagram of the media sensor of FIG. 9, with transparent media in the media path.

FIG. 11 depicts the case of transparent media 46 in the media path 44. The optical source 62 emits incident optical energy, represented by the light ray I, which passes from the sensor body 61, through the hole 45 in the upper media guide 44a, and strikes the transparent media 46. A reflected ray $R_1$ is generated, which is blocked from the optical detector 68 by the optical barrier 63, integral to the detector body 61. A transmitted ray $T_1$ emerges from the transparent media 46, is successively reflected by reflective surfaces 67a and 67b, and is directed towards the optical detector 68. Prior to reaching the optical detector 68, the optical energy $T_1$ again encounters the transparent media 46. At the lower surface of the transparent media 46, a second reflected ray $R_2$ is generated. $R_2$ is itself reflected off of reflective surface 67b, passes through the transparent media 46, and emerges as transmitted ray $T_3$, which is oriented away from the optical detector 68 and is absorbed by the optical barrier 63. Most of the optical energy in the reflected ray $T_1$ emerges from the transparent media 46, depicted as light ray $T_2$, oriented toward the optical detector 68. The optical energy $T_2$ passes through the hole 45 and impinges the optical detector 68. Due to attenuation upon twice passing through transparent media 46, the level of optical energy reaching the optical detector 68 is greater than that in the case of opaque media 46, and less than that in the case of no media present in the media path 44.

The considerations discussed above regarding preferred components, calibration, and the like are fully applicable to the media sensor 60. The media sensor 60 is operative to detect and distinguish the conditions of no media, opaque media 46, and transparent media 46 in the media path 44. In particular, in the case of no media in the media path 44, the optical detector 68 will receive a readily detectable amount of the optical energy emitted by the optical source 62. In the case of opaque media 46, the optical detector 68 will receive very little, if any, of the optical energy emitted by optical source 62. Finally, in the case of transparent media 46, the optical detector 68 will receive an attenuated level of the optical energy emitted by the optical source 62, the attenuated level being between that in the cases of opaque media 46 and no media in the media path 44. The sensor 60 is operative to separately sense the leading and trailing edges of a media sheet 46, whether it is opaque or transparent.

As referred to herein, transparent media refers to "transparencies," or media sheets commercially available and designed to be used with overhead projections and the like. The term transparent media includes translucent media. As used herein, the term normal means 90° or perpendicular. In the discussion herein, media 46 are presumed to be substantially parallel to the media path 44 at the location of the media sensor 40, 50, 60. That is, a direction normal to the media path 44 is substantially the same as a direction normal to media 46 within the media path 44.

Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the scope of the invention. The present embodiments are therefore to be construed in all aspects as illustrative and not restrictive and all changes coming within the meaning and equivalency range of the appended claims are intended to be embraced therein.

What is claimed is:

1. A method of detecting the presence and type of media in the media path of an image forming apparatus, comprising:
    directing optical energy from an optical source to an optical detector;
    directing said optical energy through at least two distinct locations along said media path;
    reflecting said optical energy off at least two reflective surfaces;
    detecting and quantifying optical energy from said optical source at said optical detector, the steps of directing optical energy from said optical source to said optical detector and detecting and quantifying optical energy from said optical source at said optical detector respectively comprising directing and receiving optical energy at substantially equal, but opposite angles with respect to a direction normal to said media path; and
    in response to detecting and quantifying said optical energy at said detector, determining whether no media, opaque media, or transparent media is present in said media path by detecting a level of optical energy in the case of transparent media that is between that in cases of opaque media and no media present.

2. The method of claim 1 wherein determining that no media is present in said media path comprises detecting a readily detectable amount of the optical energy from said source at said detector.

3. The method of claim 1 wherein determining that opaque media is present in said media path comprises detecting little or no optical energy from said source at said detector.

4. The method of claim 1 wherein determining that transparent media is present in said media path comprises detecting a level of optical energy from said source between the cases of opaque media and no media reaches said detector when transparent media is present in said media path.

5. The method of claim 1 wherein directing optical energy from said optical source to said optical detector comprises directing optical energy from said optical source disposed on a first side of said media path, through said media path a first time, to said at least two reflective surfaces disposed on a second side of said media path, through said media path a second time, to said detector disposed on said first side of said media path.

6. The method of claim 1 further comprising:
    determining the length of a media sheet by measuring the elapsed time between sensing the leading edge of said media sheet and sensing the trailing edge of said media sheet, and multiplying said elapsed time by a known speed of said media sheet.

* * * * *